US012765938B2

(12) United States Patent
Marion et al.

(10) Patent No.: US 12,765,938 B2
(45) **Date of Patent: *Oct. 20, 2026**

(54) SYSTEMS AND METHODS FOR LIMITING JOINT TEMPERATURE

(71) Applicant: ArthroCare Corporation, Austin, TX (US)

(72) Inventors: Duane W. Marion, Scottsdale, AZ (US); Katherine Knudsen, San Jose, CA (US); Robert DeCou, Redwood City, CA (US)

(73) Assignee: ArthroCare Corporation, Austin, TX (US)

( * ) Notice: Subject to any disclaimer, the term of this patent is extended or adjusted under 35 U.S.C. 154(b) by 850 days.

This patent is subject to a terminal disclaimer.

(21) Appl. No.: 17/972,748

(22) Filed: Oct. 25, 2022

(65) Prior Publication Data

US 2023/0041241 A1 Feb. 9, 2023

Related U.S. Application Data

(63) Continuation of application No. 16/540,272, filed on Aug. 14, 2019, now Pat. No. 11,510,721, which is a (Continued)

(51) Int. Cl.
*A61B 18/12* (2006.01)
*A61B 5/01* (2006.01)
(Continued)

(52) U.S. Cl.
CPC ............ *A61B 18/1233* (2013.01); *A61B 5/01* (2013.01); *A61B 18/1206* (2013.01); (Continued)

(58) Field of Classification Search
CPC .......... A61B 18/148; A61B 2018/1472; A61B 2018/162; A61B 5/01; A61M 1/0058; A61M 1/77; A61M 1/92
See application file for complete search history.

(56) References Cited

U.S. PATENT DOCUMENTS 5,409,453 A * 4/1995 Lundquist .............. A61B 10/06 607/99
5,697,536 A 12/1997 Eggers
(Continued)

FOREIGN PATENT DOCUMENTS

DE 69500422 8/1997
EP 1080680 3/2001
(Continued)

OTHER PUBLICATIONS

DE OA for 10 2009 057 921.4 dated Jul. 17, 2020, 5 pages.

*Primary Examiner* — Sean W Collins
(74) *Attorney, Agent, or Firm* — Kate Ryland Tetzlaff

(57) ABSTRACT

Limiting joint temperature. At least some of the example embodiments are systems including an electrosurgical probe and a high frequency power supply. The electrosurgical probe may include: a shaft with a distal end, a proximal end, and lumen defined within the shaft; an active electrode disposed near the distal end; a return electrode disposed on the shaft; and a temperature sensor disposed on the shaft spaced away from the active electrode and the return electrode, the temperature sensor is electrically insulated from the electrically conductive fluid. The high frequency power supply may be coupled to the active electrode, and configured to provide an electrical energy output between the active electrode and the return electrode.

17 Claims, 10 Drawing Sheets

Related U.S. Application Data continuation of application No. 15/265,049, filed on Sep. 14, 2016, now Pat. No. 10,420,601, which is a continuation of application No. 13/708,246, filed on Dec. 7, 2012, now Pat. No. 9,452,008, which is a continuation of application No. 12/333,920, filed on Dec. 12, 2008, now Pat. No. 8,355,799.

(51) Int. Cl.

| | |
|---|---|
| ***A61B 18/14*** | (2006.01) |
| *A61B 5/00* | (2006.01) |
| *A61B 17/00* | (2006.01) |
| *A61B 18/00* | (2006.01) |

(52) U.S. Cl.

CPC ............ *A61B 18/14* (2013.01); *A61B 5/4528* (2013.01); *A61B 2017/00084* (2013.01); *A61B 2018/00583* (2013.01); *A61B 2018/00702* (2013.01); *A61B 2018/00791* (2013.01); *A61B 2018/1472* (2013.01)

(56) References Cited

U.S. PATENT DOCUMENTS

| | | | | |
|---|---|---|---|---|
| 5,853,409 | A | 12/1998 | Swanson et al. | |
| 6,053,912 | A | 4/2000 | Panescu et al. | |
| 6,113,591 | A | 9/2000 | Whayne et al. | |
| 6,149,647 | A | 11/2000 | Tu et al. | |
| 6,241,724 | B1 | 6/2001 | Fleischman et al. | |
| 6,402,742 | B1 | 6/2002 | Blewett et al. | |
| 6,461,354 | B1 | 10/2002 | Olsen et al. | |
| 6,837,884 | B2 | 1/2005 | Woloszko | |
| 7,258,690 | B2 | 8/2007 | Sutton | |
| 7,347,859 | B2 | 3/2008 | Garabedian et al. | |
| 2003/0014051 | A1 * | 1/2003 | Woloszko .......... | A61B 18/1477 606/50 |
| 2003/0144656 | A1 * | 7/2003 | Ocel .................... | A61B 5/7475 606/49 |
| 2004/0186469 | A1 * | 9/2004 | Woloszko .............. | A61B 5/015 606/49 |
| 2007/0167943 | A1 | 7/2007 | Janssen et al. | |
| 2008/0082092 | A1 | 4/2008 | McPherson | |
| 2008/0082097 | A1 | 4/2008 | McPherson | |
| 2008/0147060 | A1 | 6/2008 | Choi | |
| 2008/0161797 | A1 | 7/2008 | Wang et al. | |
| 2008/0243117 | A1 | 10/2008 | Sharps et al. | |

FOREIGN PATENT DOCUMENTS

| | | |
|---|---|---|
| WO | WO9600039 | 1/1996 |
| WO | WO9634570 | 11/1996 |
| WO | WO03024506 | 3/2003 |
| WO | WO2005048809 | 6/2005 |

* cited by examiner

SYSTEMS AND METHODS FOR LIMITING JOINT TEMPERATURE

CROSS-REFERENCE TO RELATED APPLICATIONS

This application is a continuation of U.S. patent application Ser. No. 16/540,272 filed Aug. 14, 2019, entitled "SYSTEMS AND METHODS FOR LIMITING JOINT TEMPERATURE," which is a continuation of U.S. patent application Ser. No. 15/265,049 filed Sep. 14, 2016, now U.S. Pat. No. 10,420,601, issued Sep. 24, 2019, entitled "SYSTEMS AND METHODS FOR LIMITING JOINT TEMPERATURE," which is a continuation of application Ser. No. 13/708,246 filed Dec. 7, 2012, entitled "SYSTEMS AND METHODS FOR LIMITING JOINT TEMPERATURE," now U.S. Pat. No. 9,452,008, issued Sep. 27, 2016, which is a continuation of U.S. patent application Ser. No. 12/333,920 filed Dec. 12, 2008, entitled "SYSTEMS AND METHODS FOR LIMITING JOINT TEMPERATURE," now U.S. Pat. No. 8,355,799, issued Jan. 15, 2013, the disclosures of which are incorporated herein by reference in their entireties.

FIELD

The present disclosure relates to methods and apparatus for measuring temperatures at an ablation site within a body space of a patient body, such as within a joint. More particularly, the present disclosure relates to methods and apparatus for measuring temperatures of an electrically conductive fluid within a body space during ablation, such as within a joint space, without being significantly influenced by the surgical effect initiated at the active electrode.

BACKGROUND

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on external grounding of the patient, where the surgical device defines only a single electrode pole. Bipolar devices comprise both electrodes for the application of current between their surfaces.

Electrosurgical procedures and techniques are particularly advantageous since they generally reduce patient bleeding and trauma associated with cutting operations. Additionally, electrosurgical ablation procedures, where tissue surfaces and volume may be reshaped, cannot be duplicated through other treatment modalities.

Present electrosurgical techniques used for tissue ablation suffer from an inability to control the depth of necrosis in the tissue being treated. Most electrosurgical devices rely on creation of an electric arc between the treating electrode and the tissue being cut or ablated to cause the desired localized heating. Such arcs, however, often create very high temperatures causing a depth of necrosis greater than 500 μm, frequently greater than 800 μm, and sometimes as great as 1700 μm. The inability to control such depth of necrosis is a significant disadvantage in using electrosurgical techniques for tissue ablation, particularly in arthroscopic procedures for ablating and/or reshaping fibrocartilage, articular cartilage, meniscal tissue, and the like.

Generally, radiofrequency (RF) energy is extensively used during arthroscopic procedures because it provides efficient tissue resection and coagulation and relatively easy access to the target tissues through a portal or cannula. However, a typical phenomenon associated with the use of RF during these procedures is that the currents used to induce the surgical effect can result in heating of electrically conductive fluid used during the procedure to provide for the ablation and/or to irrigate the treatment site. If the temperature of this fluid were allowed to increase above a threshold temperature value, the heated fluid could result in undesired necrosis or damage to surrounding neuromuscular and/or soft tissue structures.

Previous attempts to mitigate these damaging effects have included either limiting the power output of the RF generator or to include a suction lumen on the distal tip of the electrosurgical device to continuously remove the affected fluid from the surgical site and thereby reduce the overall temperature. These solutions may be effective but are limited and they do not allow for direct feedback based upon the actual temperature of the fluid within the joint space.

There have been numerous RF based systems introduced into the market that make use of a temperature sensor in order to monitor the temperature of tissue at or near the electrode. However, these systems do not include any mechanisms to monitor the temperature of the fluid within a body space, such as a joint space.

SUMMARY

In monitoring the temperature of an electrically conductive fluid irrigating a body or joint space wherein an ablative process is occurring, one or more temperature sensors may be positioned along the probe to measure the temperature of the electrically conductive fluid itself. Such a device may comprise an electrosurgical probe having a shaft with a distal end and a proximal end, the probe further comprising an active electrode terminal disposed near the distal end, a high frequency power supply where the high frequency power supply is coupled to the active electrode terminal and a return electrode terminal, a fluid suction element for aspirating electrically conductive fluid between the active electrode terminal and the tissue, and a temperature sensor for measuring the temperature of the electrically conductive fluid where the temperature sensor may be spaced a distance away, e.g., 5 mm, from the distal tip or electrode structure.

The temperature sensor may comprise any number of sensors, e.g., thermocouple, thermistor, resistance temperature detector (RTD), etc. In particular, temperature sensor may comprise a T-type thermocouple as these sensors are well-established for use in such probes.

In use, once the electrode assembly has been desirably positioned within the body space or joint and the electrically conductive fluid has been delivered to the targeted tissue site within the body or joint space, a high frequency voltage may be applied at the electrode assembly for conduction through the electrically conductive fluid. The one or more temperature sensors positioned proximally of the electrode assembly may be used to sense a temperature of the conductive fluid itself while remaining unaffected or uninfluenced by the electrical activity from the electrodes. Optionally, the sensed temperature may be utilized to subsequently control or affect the high frequency voltage applied between the active electrode terminal and the return electrode.

To reduce or eliminate the temperature influence from an active electrode during tissue treatment, the sensor is desirably distanced from the electrode structure and may accordingly be positioned proximally along the shaft of the probe. In one example shown, the distance of the sensor removed from the electrode is at least 5 mm but may also be less than or greater than this, as practicable. With the sensor positioned accordingly, the sensor may measure the temperature of the infused electrically conductive fluid surrounding the probe and sensor as the temperature of the fluid is indicative of the temperature of the surrounding tissue or joint space within which the probe may be positioned for treatment. The fluid temperature may thus be measured without regard to the heat energy generated by the electrode structure of the probe.

The temperature sensor may be mounted directly upon the shaft although in probes having a suction lumen, the inflow and/or outflow of fluid and gas through the underlying suction lumen may affect the temperature sensed by the sensor. Thus, a thermally insulative layer such as heat shrink tubing or other insulation (e.g., comprised of thermoplastics, such as polyolefin, polyvinyl chloride (PVC), polytetrafluoroethylene (PTFE), fluorinated ethylene propylene (FEP), etc.) may be placed between the temperature sensor and outer surface of the probe. The sensor may be secured directly to the probe and/or underlying layer via another insulative layer overlying the sensor and conducting wire coupled to the sensor. The addition of the overlying layer, which may be comprised of any of the materials mentioned above, may also electrically isolate the temperature sensor from its surrounding fluid environment to prevent or inhibit electrical noise from being introduced into the temperature measurement circuit. The overlying layer may be an adhesive lined to further isolate the sensor. Additionally and/or alternatively, temperature sensor may be isolated and secured to the underlying layer by an adhesive, e.g., epoxy or cyanoacrylate glue, which may be adhered directly upon sensor.

In another embodiment, more than one sensor may be positioned around the shaft to obtain multiple readings of the fluid temperature. In yet another variation, the temperature sensor may be integrated along the probe shaft such that the sensor may be recessed along the shaft surface and the conducting wire may be passed through a lumen defined through the probe. In yet another variation, for probes having a suction lumen for withdrawing the electrically conductive fluid from the body or joint space, a temperature sensor may be alternatively positioned within the suction lumen itself.

Independently from or in addition to the temperature sensing mechanisms in or along the probe, the power source and controller may also be configured for determining, monitoring, and/or controlling a fluid temperature within the body or joint space under treatment. The one or more conducting wires from their respective temperature sensors may be routed through the cable and into electrical communication with an analog-to-digital (ADC) converter which may convert the output of the temperature sensor to a digital value for communication with the microcontroller. The measured and converted temperature value may be compared by the microcontroller to a predetermined temperature limit pre-programmed or stored within the microcontroller such that if the measured temperature value of the body or joint space exceeds this predetermined limit, an alarm or indicator may be generated and/or the RF output may be disabled or reduced. Additionally and/or alternatively, the microcontroller may be programmed to set a particular temperature limit depending upon the type of device that is coupled to the controller.

Furthermore, the microcontroller may also be programmed to enable the user to select from specific tissue or procedure types, e.g., ablation of cartilage or coagulation of soft tissues, etc. Each particular tissue type and/or procedure may have a programmed temperature limit pre-set in advance depending upon the sensitivity of the particular anatomy to injury due to an elevation in fluid temperature.

In additional embodiments, the microcontroller may be programmed to monitor the exposure of a body or joint space to a specific elevated fluid temperature level rather than limiting the treatment temperature upon the instantaneous measured temperature value. For example, as the fluid temperature increases during treatment, tissue necrosis typically occurs more rapidly; thus, the microcontroller may be programmed to generate an alarm or indication based upon a combination of time-temperature exposure.

In yet another embodiment, the microcontroller may be programmed to incorporate a set of multiple progressive temperature limits. A first temperature limit may be programmed whereby if the measured temperature rise of fluid irrigating the body or joint space exceeds the first limit, an alarm or indication may be automatically generated by the microcontroller to alert the user. A second temperature limit may also be programmed whereby if the measured temperature of fluid irrigating the body or joint space exceeded the second limit, the microcontroller may be programmed to reduce or deactivate the RF output of the electrode to mitigate the risk of injury to the patient.

Additionally and/or alternatively, the controller may be further configured to interface directly with a fluid pump which may be configured to provide control of both electrically conductive fluid in-flow to the body or joint space as well as out-flow from the body or joint space. The measured temperature within the body or joint space may be monitored and utilized as a control parameter for the fluid pump whereby the fluid in-flow and/or out-flow may be regulated to maintain a temperature of the fluid irrigating the body or joint space within a specified range or below a temperature limit where potential injury could occur.

DETAILED DESCRIPTION

Figure 1:
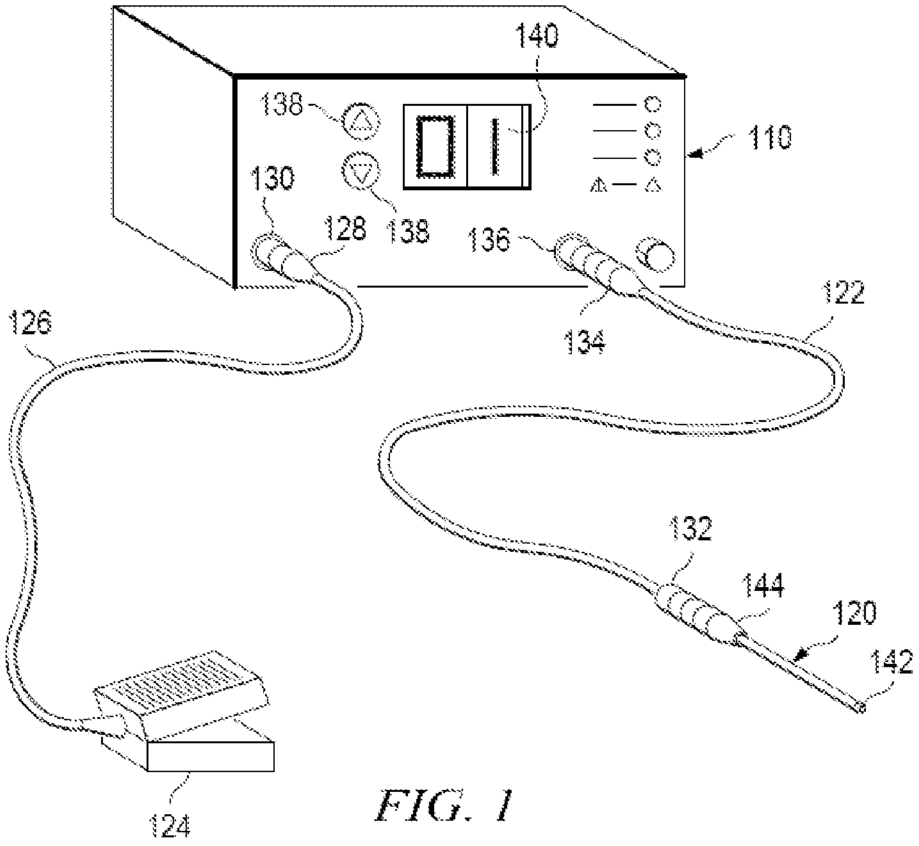
FIG. 1 is a perspective view of the electrosurgical system including an electrosurgical probe and electrosurgical power supply.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

The treatment device of the present invention may have a variety of configurations. However, one variation of the device employs a treatment device using Coblation® technology.

The assignee of the present invention developed Coblation® technology. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a liquid or gas, such as isotonic saline, blood, extracelluar or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer. Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of this phenomena can be found in commonly assigned U.S. Pat. No. 5,697,882, the complete disclosure of which is incorporated herein by reference.

In some applications of the Coblation® technology, high frequency (RF) electrical energy is applied in an electrically conducting media environment to shrink or remove (i.e., resect, cut, or ablate) a tissue structure and to seal transected vessels within the region of the target tissue. Coblation® technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue.

The amount of energy produced by the Coblation® device may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the Coblation device may be configured to produce energy sufficient to break the molecular bonds of certain tissue but insufficient to break the molecular bonds of other tissue. For example, fatty tissue (e.g., adipose) has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomena can be found in commonly assigned U.S. Pat. Nos. 6,355,032; 6,149,120 and 6,296,136, the complete disclosures of which are incorporated herein by reference.

The active electrode(s) of a Coblation® device may be supported within or by an inorganic insulating support positioned near the distal end of the instrument shaft. The return electrode may be located on the instrument shaft, on another instrument or on the external surface of the patient (i.e., a dispersive pad). The proximal end of the instrument (s) will include the appropriate electrical connections for coupling the return electrode(s) and the active electrode(s) to a high frequency power supply, such as an electrosurgical generator.

In one example of a Coblation® device for use with the embodiments disclosed herein, the return electrode of the device is typically spaced proximally from the active electrode(s) a suitable distance to avoid electrical shorting between the active and return electrodes in the presence of electrically conductive fluid. In many cases, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode may have an exposed length in the range of about 1 mm to 20 mm.

A Coblation® treatment device for use according to the present embodiments may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The Coblation® device is not limited to electrically isolated active electrodes, or even to a plurality of active electrodes. For example, the array of active electrodes may be connected to a single lead that extends through the catheter shaft to a power source of high frequency current.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck.

The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation.)

The peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with, e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The power source may deliver a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly frequencies around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, the complete disclosure of both patents are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 μH to 50,000 μH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

Moreover, other treatment modalities (e.g., laser, chemical, other RF devices, etc.) may be used in the inventive method either in place of the Coblation® technology or in addition thereto.

Referring now to FIG. 1, an exemplary electrosurgical system for resection, ablation, coagulation and/or contraction of tissue will now be described in detail. As shown, certain embodiments of the electrosurgical system generally include an electrosurgical probe 120 connected to a power supply 110 for providing high frequency voltage to one or more electrode terminals on probe 120. Probe 120 includes a connector housing 144 at its proximal end, which can be removably connected to a probe receptacle 132 of a probe cable 122. The proximal portion of cable 122 has a connector 134 to couple probe 120 to power supply 110 at receptacle 136. Power supply 110 has an operator controllable voltage level adjustment 138 to change the applied voltage level, which is observable at a voltage level display 140. Power supply 110 also includes one or more foot pedals 124 and a cable 126 which is removably coupled to a receptacle 130 with a cable connector 128. The foot pedal 124 may also include a second pedal (not shown) for remotely adjusting the energy level applied to electrode terminals 142, and a third pedal (also not shown) for switching between an ablation mode and a coagulation mode.

Figure 2:
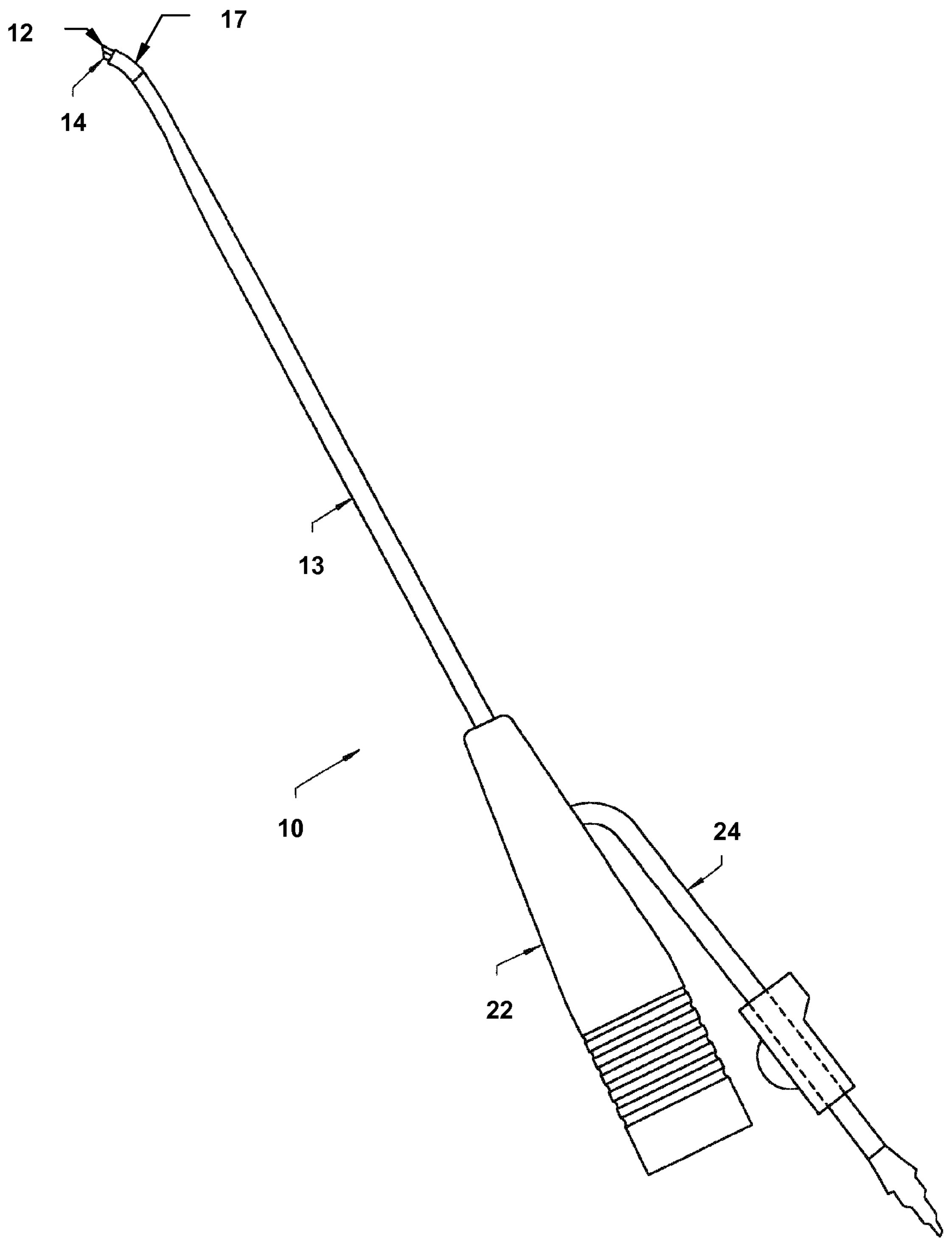
FIG. 2 is side view of an electrosurgical probe according to the present embodiments.

Referring now to FIG. 2, an electrosurgical probe 10 representative of the currently described embodiments includes an elongate shaft 13 which may be flexible or rigid, a handle 22 coupled to the proximal end of shaft 13 and an electrode support member 14 coupled to the distal end of shaft 13. Probe 10 includes an active electrode terminal 12 disposed on the distal tip of shaft 13. Active electrode 12 may be connected to an active or passive control network within a power supply and controller 110 (see FIG. 1) by means of one or more insulated electrical connectors (not shown). The active electrode 12 is electrically isolated from a common or return electrode 17 which is disposed on the shaft proximally of the active electrode 12, preferably being within 1 mm to 25 mm of the distal tip. Proximally from the distal tip, the return electrode 17 is generally concentric with the shaft of the probe 10. The support member 14 is positioned distal to the return electrode 17 and may be composed of an electrically insulating material such as epoxy, plastic, ceramic, glass or the like. Support member 14 extends from the distal end of shaft 13 (usually about 1 to 20 mm) and provides support for active electrode 12.

Figure 3:
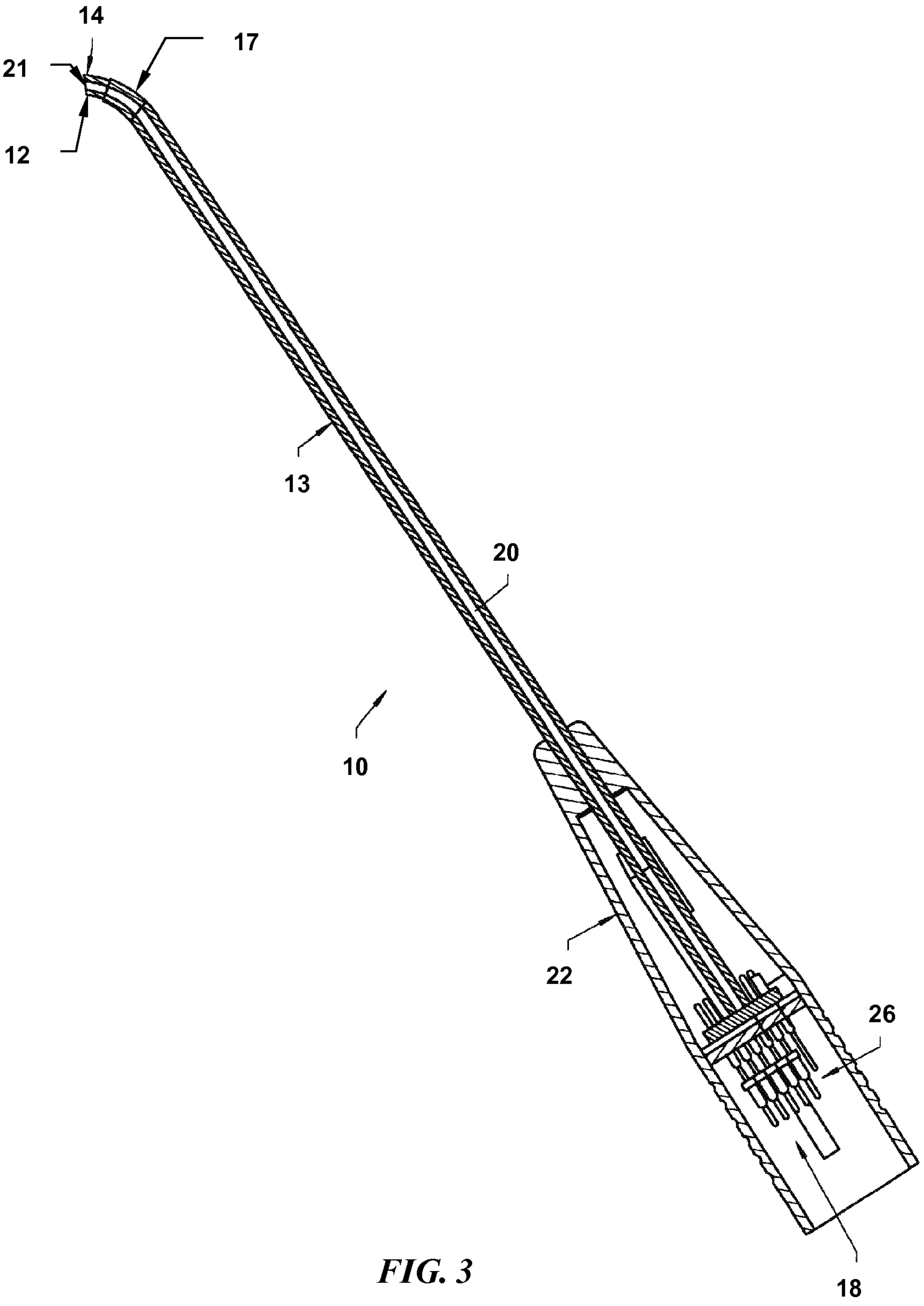
FIG. 3 is a cross-sectional view of the electrosurgical probe of FIG. 2.

Referring now to FIG. 3, probe 10 may further include a suction lumen 20 for aspirating excess fluids, bubbles, tissue fragments, and/or products of ablation from the target site. Suction lumen 20 extends through support member 14 to a distal opening 21, and extends through shaft 13 and handle 22 to an external connector 24 (see FIG. 2) for coupling to a vacuum source. Typically, the vacuum source is a standard hospital pump that provides suction pressure to connector 24 and suction lumen 20. Handle 22 defines an inner cavity 18 that houses electrical connections 26 and provides a suitable interface for electrical connection to power supply/controller 110 via an electrical connecting cable 122 (see FIG. 1).

In certain embodiments, active electrode 12 may comprise an active screen electrode 40. Screen electrode 40 may have a variety of different shapes, such as the shapes shown in FIGS. 4A and 4B. Electrical connectors 48 (see FIG. 9) extend from connections 26 through shaft 13 to screen electrode 40 to electrically couple the active screen electrode 40 to the high frequency power supply 110 (see FIG. 1). Screen electrode 40 may comprise a conductive material, such as tungsten, titanium, molybdenum, platinum, or the like. Screen electrode 40 may have a diameter in the range of about 0.5 to 8 mm, preferably about 1 to 4 mm, and a thickness of about 0.05 to about 2.5 mm, preferably about 0.1 to 1 mm. Screen electrode 40 may comprise a plurality of apertures 42 configured to rest over the distal opening 21 of suction lumen 20. Apertures 42 are designed to allow for the passage of aspirated excess fluids, bubbles, and gases from the ablation site and are typically large enough to allow ablated tissue fragments to pass through into suction lumen 20. As shown, screen electrode 40 has a generally irregular shape which increases the edge to surface-area ratio of the screen electrode 40. A large edge to surface-area ratio increases the ability of screen electrode 40 to initiate and maintain a plasma layer in conductive fluid because the edges generate higher current densities, which a large surface area electrode tends to dissipate power into the conductive media.

Figure 4A:
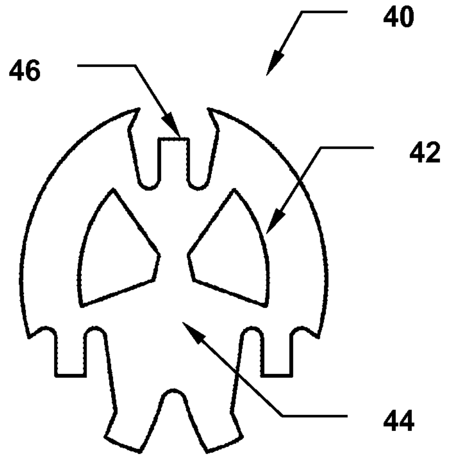
FIG. 4A is a perspective view of an embodiment of the active electrode for the probe of FIGS. 1 and 2.
Figure 4B:
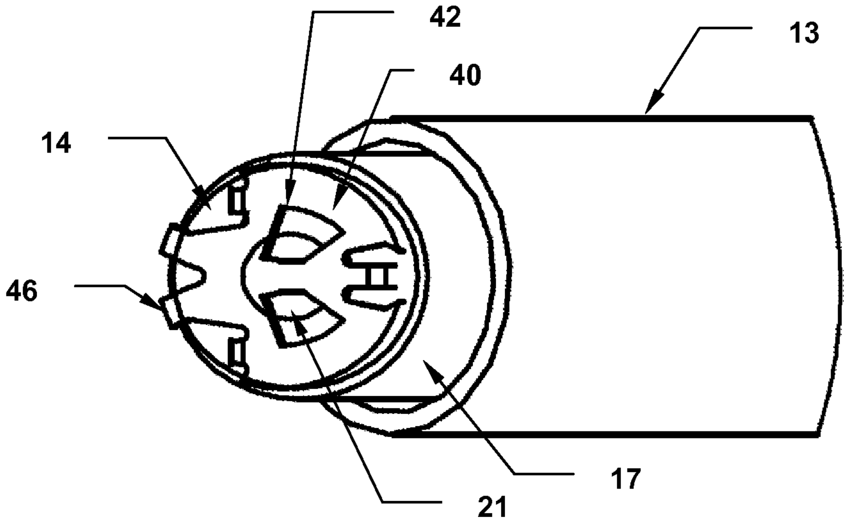
FIG. 4B is a detailed view of the distal tip of the electrosurgical probe of FIGS. 1 and 2 incorporating the active screen electrode of FIG. 4A.

In the representative embodiment shown in FIGS. 4A and 4B, screen electrode 40 includes a body 44 that rests over insulative support member 14 and the distal opening 21 to suction lumen 20. Screen electrode 40 further comprises at least five tabs 46 that may rest on, be secured to, and/or be embedded in insulative support member 14. In certain embodiments, electrical connectors 48 (see FIG. 9) extend through insulative support member 14 and are coupled (i.e., via adhesive, braze, weld, or the like) to one or more of tabs 46 in order to secure screen electrode 40 to the insulative support member 14 and to electrically couple screen electrode 40 to power supply 110 (see FIG. 1). Preferably, screen electrode 40 forms a substantially planar tissue treatment surface for smooth resection, ablation, and sculpting of the meniscus, cartilage, and other soft tissues. In reshaping cartilage and meniscus, the physician often desires to smooth the irregular, ragged surface of the tissue, leaving behind a substantially smooth surface. For these applications, a substantially planar screen electrode treatment surface is preferred.

Further details and examples of instruments which may be utilized herein are described in detail in U.S. Pat. Nos. 6,254,600; 6,557,559 and 7,241,293 which are incorporated herein by reference in their entirety.

Figure 5:
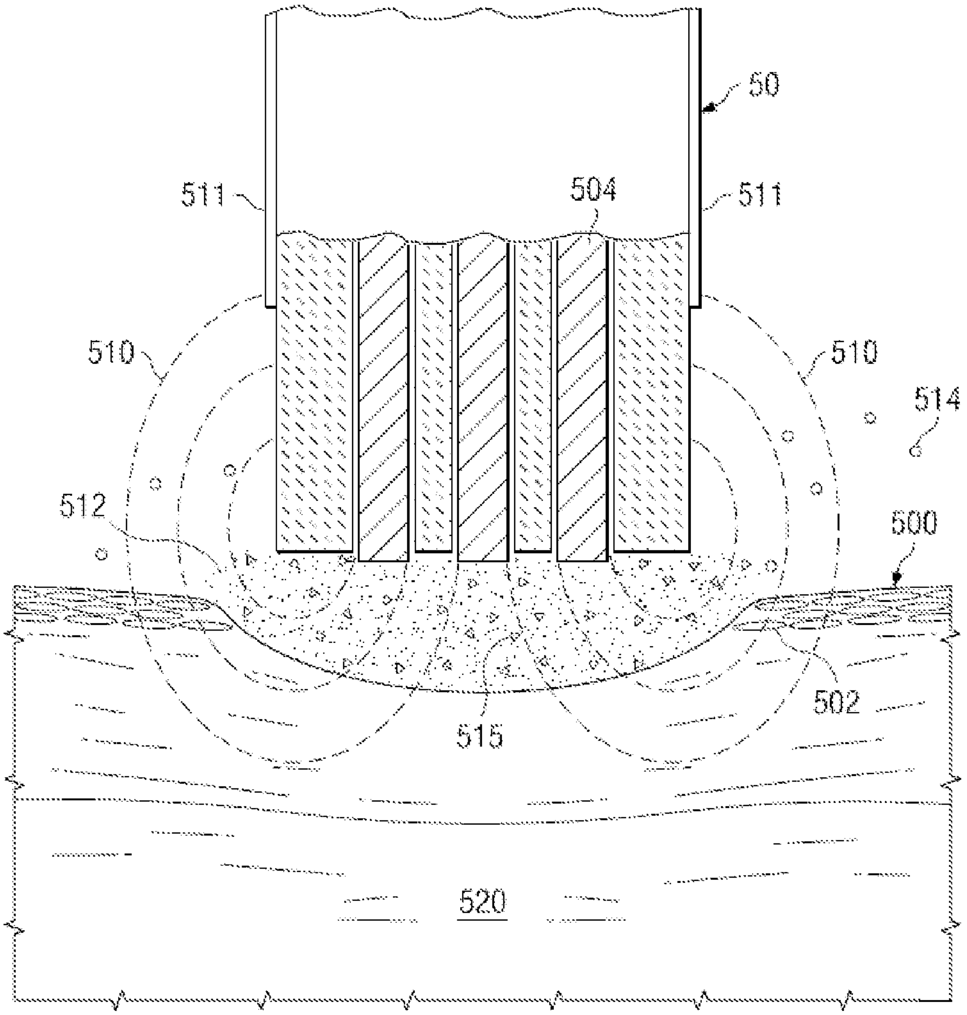
FIG. 5 illustrates a detailed view illustrating ablation of tissue.

FIG. 5 representatively illustrates in more detail the removal of a target tissue by use of an embodiment of a representative electrosurgical probe 50 according to the present disclosure. As shown, the high frequency voltage is sufficient to convert the electrically conductive fluid (not shown) between the target tissue 502 and active electrode terminal(s) 504 into an ionized vapor layer 512 or plasma. As a result of the applied voltage difference between electrode terminal(s) 504 and the target tissue 502 (i.e., the voltage gradient across the plasma layer 512), charged particles 515 in the plasma are accelerated. At sufficiently high voltage differences, these charged particles 515 gain sufficient energy to cause dissociation of the molecular bonds within tissue structures in contact with the plasma field. This molecular dissociation is accompanied by the volumetric removal (i.e., ablative sublimation) of tissue and the production of low molecular weight gases 514, such as oxygen, nitrogen, carbon dioxide, hydrogen and methane. The short range of the accelerated charged particles 515 within the tissue confines the molecular dissociation process to the surface layer to minimize damage and necrosis to the underlying tissue 520.

During the process, the gases 514 will be aspirated through a suction opening and suction lumen to a vacuum source (not shown). In addition, excess electrically conductive fluid, and other fluids (e.g., blood) will be aspirated from the target site 500 to facilitate the surgeon's view. During ablation of the tissue, the residual heat generated by the current flux lines 510 (typically less than 150 degree C.) between electrode terminals 504 and return electrode 511 will usually be sufficient to coagulate any severed blood vessels at the site. If not, the surgeon may switch the power supply (not shown) into the coagulation mode by lowering the voltage to a level below the threshold for fluid vaporization, as discussed above. This simultaneous hemostasis results in less bleeding and facilitates the surgeon's ability to perform the procedure.

Figure 6A:
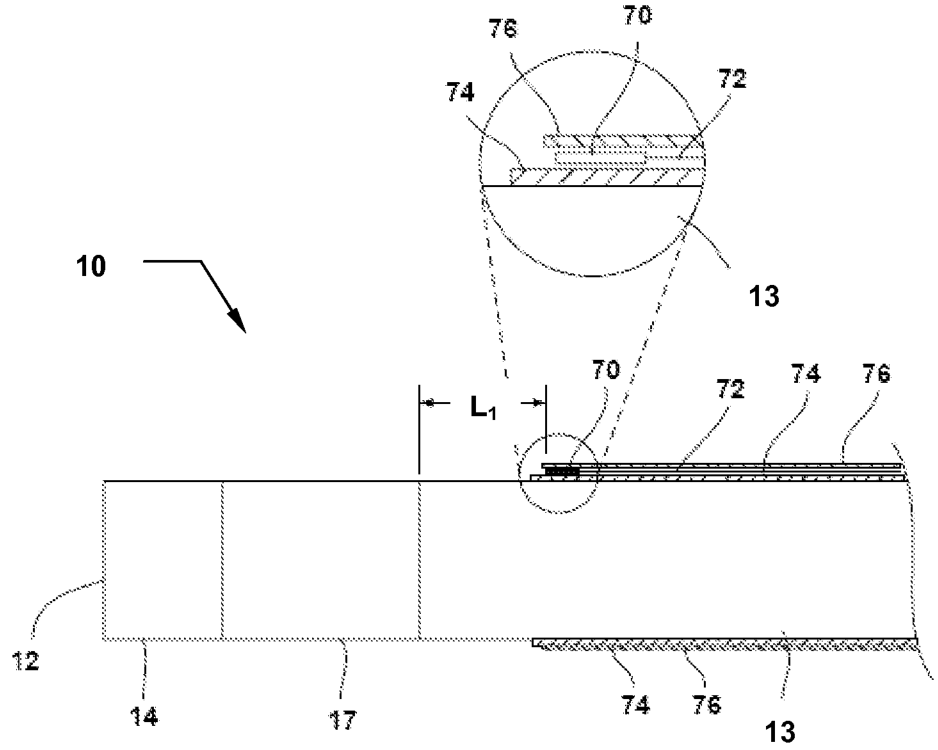
FIG. 6A is a partial cross-sectional side view of a temperature sensor positioned along the shaft of an electrosurgical probe proximally of the electrode assembly.

Because of the energy generated and applied during treatment within the patient body with the above-described probe 10 or other variations thereof, difficulties arise in determining, monitoring, and/or limiting the actual temperature of electrically conductive fluid irrigating the treated body space, joint, or tissue region. Accordingly, probe 10 may include mechanisms for measuring a temperature of the electrically conductive fluid itself without being overly influenced by the surgical effect occurring at the active electrode 12. Turning to FIG. 6A, one embodiment is illustrated in the side view of probe 10 and the detail side view showing a temperature sensor 70 positioned along the probe shaft proximally of the return electrode 17. Temperature sensor 70 may comprise any number of sensors, e.g., thermocouple, thermistor, resistance temperature detector (RTD), etc. In particular, temperature sensor 70 may comprise a T-type thermocouple as these sensors are well-established for use in such probes.

To reduce or eliminate the temperature-monitoring influence from an active electrode 12 during tissue treatment, sensor 70 is desirably distanced from both the active electrode 12 and return electrode 17 and may accordingly be positioned proximally along the shaft 13 of probe 10. In the example shown, the distance L.sub.1 of sensor 70 removed from return electrode 17 is at least 5 mm but may also be less than or greater than this distance, as practicable. With sensor 70 positioned accordingly, the sensor 70 may measure the temperature of the infused electrically conductive fluid/irrigant surrounding the probe 10 and sensor 70 as the temperature of the fluid is indicative of the temperature of the surrounding tissue or joint space within which probe 10 may be positioned for treatment. The fluid temperature may thus be measured without regard to any energy generated by the current traveling between active electrode 12 and return electrode 17 of probe 10.

Temperature sensor 70 may be mounted directly upon the shaft. However, certain embodiments of probe 10 may have a suction lumen (see FIG. 3) for aspirating fluid and ablative byproducts from the treatment site, wherein the inflow and/or outflow of fluid and gas through the underlying suction lumen may affect the temperature sensed by sensor 70. Thus, a thermally insulative layer 74 such as heat shrink tubing or other insulation (e.g., comprised of thermoplastics, such as polyolefin, polyvinyl chloride (PVC), polytetrafluoroethylene (PTFE), fluorinated ethylene propylene (FEP), etc.) may be placed between the temperature sensor 70 and outer surface of shaft 13. Sensor 70 may be secured directly to the shaft 13 and/or underlying layer 74 via another insulative layer 76 overlying sensor 70 and conducting wire 72 coupled to sensor 70. The addition of the overlying layer 76, which may be comprised of any of the materials mentioned above, may also electrically isolate temperature sensor 70 from its surrounding saline environment to prevent or inhibit electrical noise from being introduced into the temperature measurement circuit. Overlying layer 76 may be adhesive lined to further isolate the sensor 70.

Figure 6B:
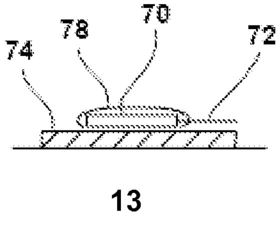
FIG. 6B is a detail cross-sectional side view of a temperature sensor insulated via an adhesive.

Additionally and/or alternatively, temperature sensor 70 may be isolated and secured to the underlying layer 74 by an adhesive 78, e.g., epoxy or cyanoacrylate glue, which may be adhered directly upon sensor 70, as illustrated in the detail side view of FIG. 6B.

Figure 7:
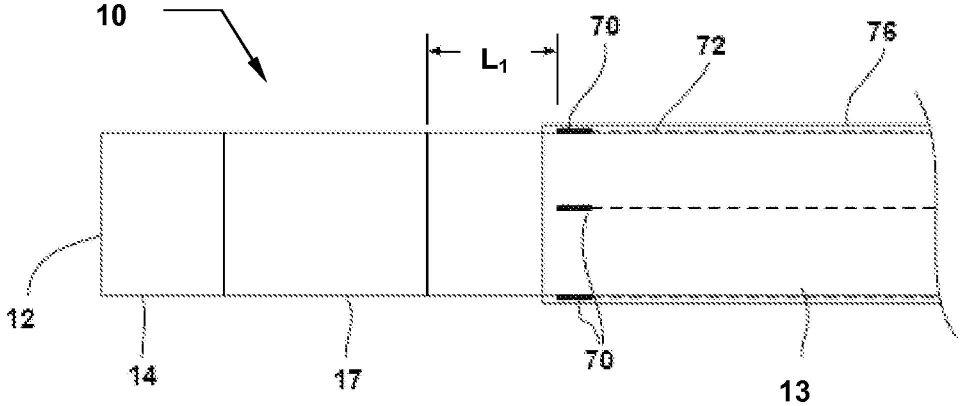
FIG. 7 is a side view of another variation where multiple temperature sensors may be positioned about the shaft of an electrosurgical probe proximally of the electrode assembly.

In another embodiment, a side view of FIG. 7 shows a variation where multiple temperature sensors 70, e.g., greater than one sensor, may be positioned around the shaft 13 to obtain multiple readings of the fluid temperature. Although the multiple temperature sensors 70 may be uniformly positioned relative to one another about a circumference of shaft 13, they may be alternatively positioned at arbitrary locations as well. Moreover, each of the multiple sensors 70 may be positioned at differing distances L.sub.1 along shaft 13 from return electrode 17. In sensing the multiple fluid temperatures, each of the temperatures may be displayed to the user and/or alternatively they may be calculated to present an average temperature value to the user.

Figure 8:
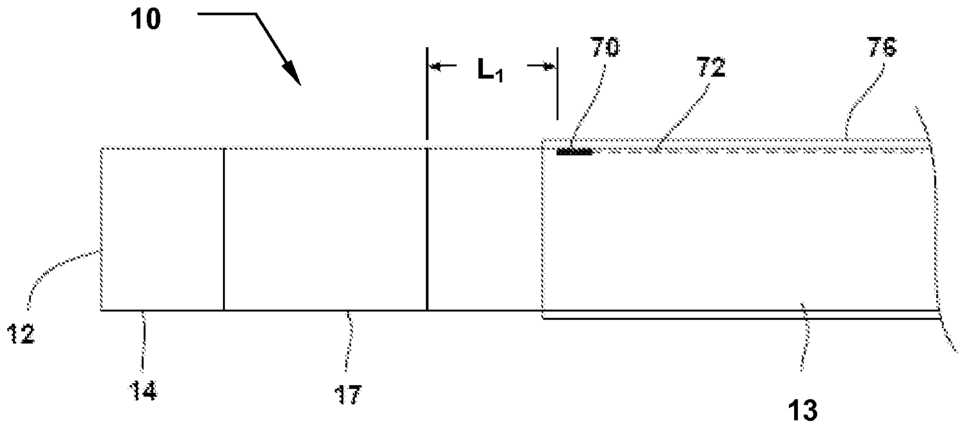
FIG. 8 is a side view of yet another variation in which a temperature sensor may be integrated along the shaft of an electrosurgical probe.

In yet another variation, a side view of FIG. 8 shows another variation where temperature sensor 70 may be integrated along the shaft 13 such that sensor 70 may be recessed along the shaft surface and conducting wire 72 may be passed through a lumen (not shown) defined through probe 10. Sensor 70 may still be insulated from the shaft 13 and may also be insulated as described above.

Figure 9:
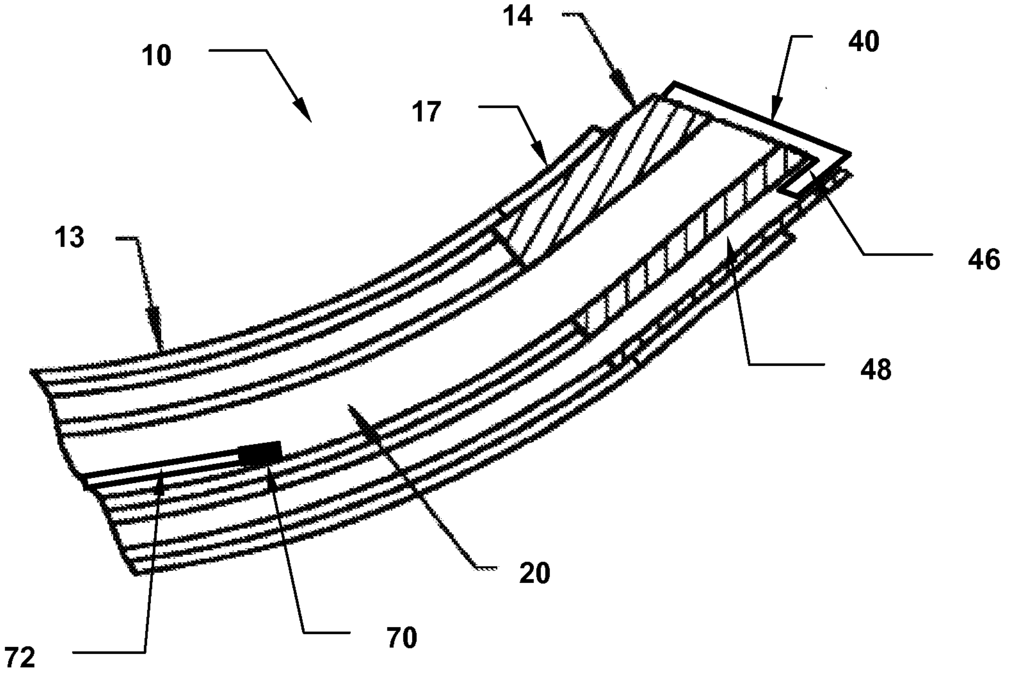
FIG. 9 is a side view of yet another variation where a temperature sensor may be positioned within a fluid lumen of an electrosurgical probe to sense the fluid temperature immediately removed from the vicinity of the active electrode.

Referring now to FIG. 9, in yet another variation a representative probe 10 having a suction lumen 20 for aspirating electrically conductive fluid from the body or joint space, a temperature sensor 70 and conducting wire 72 may be alternatively positioned within the suction lumen 20 itself, as illustrated in the detail cross-sectional view of FIG. 9. In this example, a temperature of the electrically conductive fluid recently in the immediate vicinity of the active screen electrode 40 and then aspirated into suction lumen 20 may be measured as one method for determining a temperature-effect induced in nearby tissues due to the electrosurgical procedure. Such temperature measurements could be used to control the RF output in order to provide therapies where it may be desirable to elevate the temperature of the target tissue to a specific temperature range. This configuration may also yield temperature data that may be used to directly correlate the temperature of the target tissue from the aspirated conductive fluid/irrigant and thereby allow the user to get direct feedback of the actual temperature of the tissue and/or limit the RF output depending on preset limits or for a given procedure or tissue type.

Figure 10:
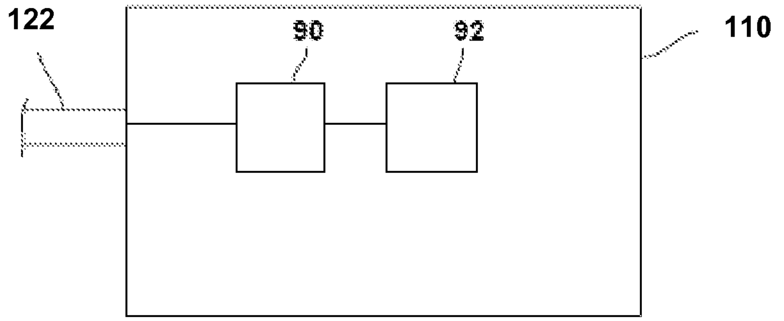
FIG. 10 is a schematic representation of a microcontroller within the controller which is coupled to the temperature sensor.

Independently from or in addition to the temperature sensing mechanisms in or along the probe 10, the power supply/controller 110 may also be configured for determining and/or controlling a fluid temperature within the body or joint space under treatment. FIG. 10 shows a representative schematic of controller 110 with cable 122 coupled thereto. The one or more conducting wires from their respective temperature sensors may be routed through cable 122 and into electrical communication with analog-to-digital (ADC) converter 90 which may convert the output of the temperature sensor to a digital value for communication with microcontroller 92. The measured and converted temperature value may be compared by microcontroller 92 to a predetermined temperature limit pre-programmed or stored within microcontroller 92 such that if the measured temperature value of the conductive fluid irrigating the body or joint space exceeds this predetermined limit, an alarm or indicator may be generated and/or the RF output may be disabled or reduced. Additionally and/or alternatively, the microcontroller 92 may be programmed to set a particular temperature limit depending upon the type of device that is coupled to controller 110.

Furthermore, microcontroller 92 may also be programmed to allow the user to select from specific tissue or procedure types, e.g., ablation of cartilage or coagulation of soft tissues, etc. Each particular tissue type and/or procedure may have a programmed temperature limit pre-set in advance depending upon the sensitivity of the particular anatomy to injury due to an elevation in temperature.

Figure 11:
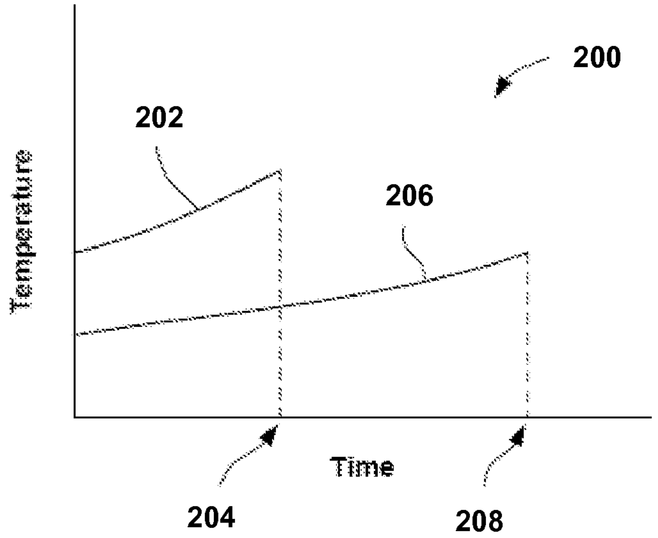
FIG. 11 is an illustrative graph showing how the microcontroller may be programmed comparing treatment time versus temperature.

In additional variations, the microcontroller 92 may be programmed to monitor the exposure of a body or joint space to a specific elevated fluid temperature level rather than limiting the treatment temperature upon the instantaneous measured temperature value. For example, as the fluid treatment temperature increases, tissue necrosis typically occurs more rapidly; thus, microcontroller 92 may be programmed to generate an alarm or indication based upon a combination of time-temperature exposure. An exemplary chart 200 is illustrated in FIG. 11 which shows first temperature plot 202 indicating treatment of a body or joint space exposed to a irrigating conductive fluid at a first elevated temperature level. Because of the relatively elevated fluid treatment temperature, the treatment time may be limited to a first predetermined time 204 by microcontroller 92 which may shut off or reduce the power level automatically. This is compared to second temperature plot 206 indicating treatment of a body or joint space exposed to a irrigating conductive fluid at a second elevated temperature level which is less than first temperature plot 202. Because of the lower relative temperature, tissue necrosis may occur at a relatively slower rate allowing the treatment time to be extended by microcontroller 92 to a relative longer time period to second predetermined time 208.

Figure 12:
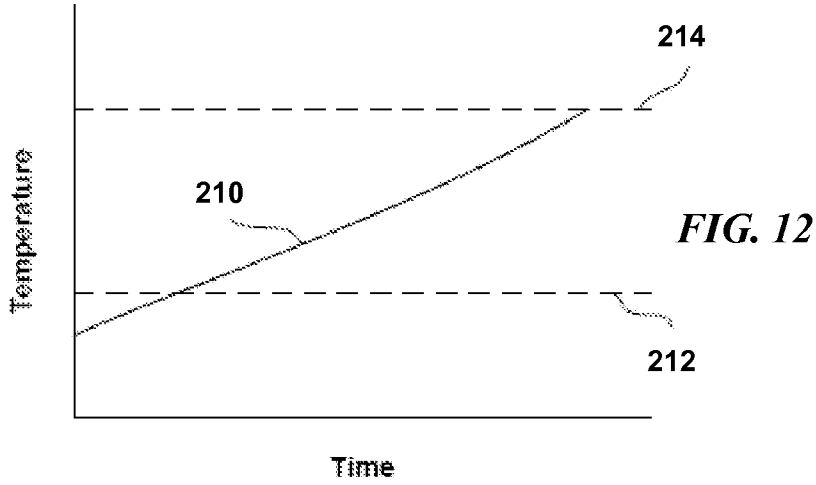
FIG. 12 is an illustrative graph showing how the microcontroller may be programmed to indicate an alarm at a first temperature threshold and to cease further power upon the temperature reaching a second temperature threshold.

In yet another variation, microcontroller 92 may be programmed to incorporate a set of multiple progressive temperature limits, as shown in the exemplary chart of FIG. 12. A first temperature limit 212 may be programmed whereby if the measured temperature rise 210 of the irrigating conductive fluid in the body or joint space exceeded first limit 212, an alarm or indication may be automatically generated by microcontroller 92 to alert the user. A second temperature limit 214 may also be programmed whereby if the measured temperature 210 of the irrigating conductive fluid in the body or joint space exceeded the second limit 214, microcontroller 92 may be programmed to reduce or deactivate the RF output of active electrode 12 to mitigate the risk of injury to the patient.

Figure 13:
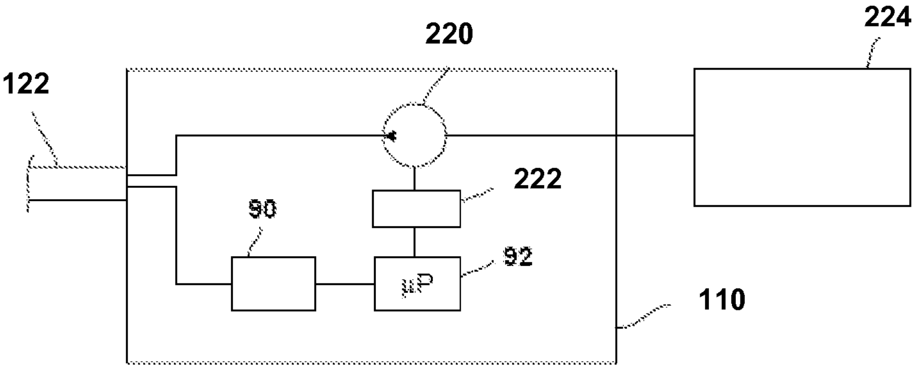
FIG. 13 is a schematic representation of a microcontroller and a fluid pump which may be used to control the inflow or outflow of fluids through an electrosurgical probe to control temperature.

Additionally and/or alternatively, controller 110 may be further configured to interface directly with a fluid pump, e.g., an arthroscopy saline pump 220 which provides a controlled in-flow of electrically conductive fluid (e.g., saline) to the body or joint space. Such a fluid pump 220 may be configured to provide control of both electrically conductive fluid in-flow to the body or joint space as well as out-flow from the body or joint space, as shown in the schematic illustration of FIG. 13. As illustrated, pump 220 may be electrically coupled to pump controller 222 which in turn may be in communication with microcontroller 92. Pump 220 may be further fluidly coupled to fluid reservoir 224 which holds the electrically conductive fluid and/or an empty reservoir (not shown) for receiving evacuated electrically conductive fluid from the body or joint space.

Figure 14A:
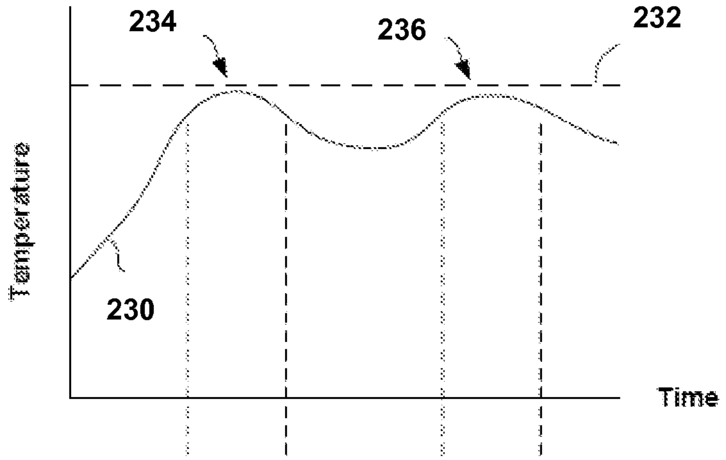
FIG. 14A is an illustrative graph showing measured temperature rise and decline as the flow rate of the fluid is varied.
Figure 14B:
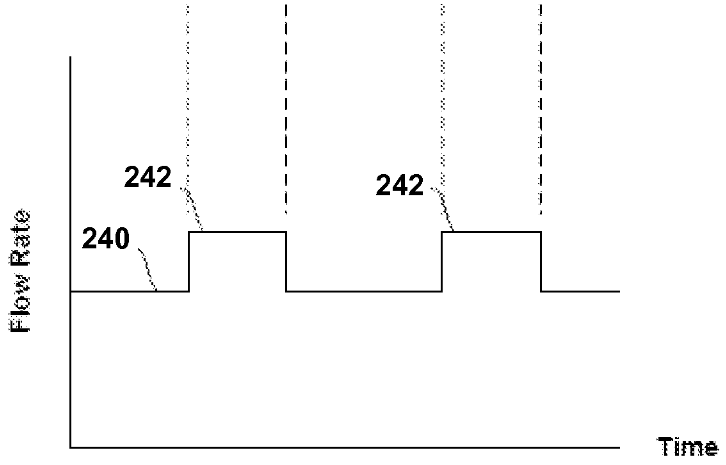
FIG. 14B is an illustrative graph showing increases in flow rate based upon the sensed temperature.

The measured temperature 230 of fluid within the body or joint space may be monitored and utilized as a control parameter for the fluid pump 220 whereby the fluid in-flow and/or out-flow may be regulated to maintain a temperature of the body or joint space within a specified range or below a temperature limit where potential injury could occur. An example of this is illustrated in the chart of FIG. 14A, which shows the measured temperature 230 of fluid within the body or joint space increasing towards a pre-programmed temperature limit 232. Once the measured temperature 230 has approached 234, 236 or exceeded this limit 232, the fluid pump 220 flow rate may be automatically increased by microcontroller 92 from a first pump flow rate 240 to a second increased flow rate 242 until the measured temperature 230 decreases, at which point the pump flow rate may be automatically decreased to the first pump flow rate 240, as indicated in FIG. 14B. This temperature moderation may be continued by cycling the flow rates between an initial level and an increased level for the duration of the procedure if so desired. Alternatively, the out-flow rate may be increased to remove any heated fluid to lower the temperature of fluid within the body or joint space.

Other modifications and variations can be made to the disclosed embodiments without departing from the subject invention. For example, other uses or applications are possible. Similarly, numerous other methods of controlling or characterizing instruments or otherwise treating tissue using electrosurgical probes will be apparent to the skilled artisan. Moreover, the instruments and methods described herein may be utilized in instruments for various regions of the body (e.g., shoulder, knee, etc.) and for other tissue treatment procedures (e.g., chondroplasty, menectomy, etc.). Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

While preferred embodiments of this invention have been shown and described, modifications thereof can be made by one skilled in the art without departing from the scope or teaching herein. The embodiments described herein are exemplary only and are not limiting. Because many varying and different embodiments may be made within the scope of the present teachings, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. A system for treating tissue at a target site within a body or joint space, the system comprising:

an active electrode at a distal end of an electrosurgical probe;

a means for supporting the active electrode, the active electrode disposed at a distal end of the means for supporting;

a return electrode, the return electrode disposed at a proximal end of the means for supporting;

a means for gripping the electrosurgical probe;

a means for holding the active electrode, the return electrode, and the means for supporting at a displaced location from the means for gripping, the means for holding defines a proximal end at the means for gripping and a distal end;

a means for measuring temperature disposed along the means for holding, the means for measuring temperature disposed between the return electrode and the means for gripping; and a means for electrically insulating the means for measuring temperature from electrically conductive fluid within the body or joint space.

2. The system of claim 1 wherein the means for measuring temperature is disposed at at least one location selected from a group comprising: at least 5 mm away from the distal end of the means for holding; and between 3 mm and 20 mm, inclusive, away from the distal end of the means for holding.

3. The system of claim 1 wherein the means for measuring temperature is at least one selected from a group comprising: a thermocouple; a T type thermocouple; a thermistor; and a resistance detector.

4. The system of claim 1 wherein the means for supporting is composed of an electrically insulating material.

5. The system of claim 1 further comprising a means for thermally insulating the means for measuring temperature, the means for thermally insulating disposed between the means for measuring temperature and the means for holding.

6. The system of claim 1 further comprising:

a first means for conveying aspirated fluid through the means for supporting; and a second means for conveying aspirated fluid through the means for holding, the second means for conveying fluidly coupled to the first means for conveying.

7. The system of claim 1 wherein the means for measuring temperature further comprises:

a first means for measuring temperature at a first radial location on the means for holding; and a second means for measuring temperature at a second radial location on the means for holding.

8. The system of claim 7 wherein the first means for measuring temperature and the second means for measuring temperature are disposed at least 5 mm away from the distal end of the means for holding.

9. A method for treating tissue comprising:

a step for positioning a distal end of an electrosurgical instrument adjacent to a target site in a patient's body or joint space;

a step for circulating an electrically conductive fluid through the target site;

a step for ablating tissue at the target site, the step for ablating raises temperature of the electrically conductive fluid at the target site; and a step for measuring temperature of the electrically conductive fluid at a location electrically insulated from the electrically conductive fluid, and thermally insulated from the electrically conductive fluid aspirated from the target site.

10. The method of claim 9 wherein the step for measuring further comprises a step for measuring temperature of the electrically conductive fluid at a location between 3 mm and 20 mm, inclusive, away from a distal end of the electrosurgical instrument.

11. The method of claim 9 wherein the step for measuring temperature further comprises a step for measuring temperature of the electrically conductive fluid at a location at least 5 mm away from a distal end of the electrosurgical instrument.

12. The method of claim 9 wherein the step for measuring further comprises a step for measuring a plurality of temperatures of the electrically conductive fluid in the joint space during the step for ablating.

13. The method of claim 12 wherein the step for measuring a plurality of temperatures further comprises:

a first step for measuring temperature at a first radial location, the first radial location between 3 mm and 20 mm, inclusive, away from a distal end of the electrosurgical instrument; and a second step for measuring temperature at a second radial location, different than the first radial location, the second radial location between 3 mm and 20 mm, inclusive, away from the distal end of the electrosurgical instrument.

14. An electrosurgical probe comprising:

a handpiece;

an elongate shaft coupled to the handpiece;

a return electrode disposed at a distal end of the elongate shaft;

an insulative support disposed distal to the return electrode;

an active electrode at a distal end of the insulative support; and a means for measuring temperature of electrically conductive fluid, the means located on the elongate shaft between the return electrode and the handpiece wherein the means for measuring temperature further comprises a means for electrically insulating the means for measuring temperature from electrically conductive fluid.

15. The electrosurgical probe of claim 14 wherein the means for measuring temperature is disposed at a location being at least one selected from a group comprising: at least 5 mm away from the distal end of the elongate shaft; and between 3 mm and 20 mm, inclusive, away from the distal end of the elongate shaft.

16. The electrosurgical probe of claim 14 wherein the means for measuring temperature is at least one selected from a group comprising: a thermocouple; a T type thermocouple; a thermistor; and a resistance detector.

17. The electrosurgical probe of claim 14 further comprising a means for thermally insulating the means for measuring temperature, the means for thermally insulating disposed between the means for measuring temperature and a suction lumen through the elongate shaft.

* * * * *